US010231680B2

(12) United States Patent
Coppens et al.

(10) Patent No.: US 10,231,680 B2
(45) Date of Patent: Mar. 19, 2019

(54) HEAT FORMABLE PATIENT POSITIONING CUSHION, METHOD OF PRODUCING A HEAT FORMABLE PATIENT POSITIONING CUSHION, AND HEAT FORMABLE PATIENT POSITIONING SYSTEM

(71) Applicant: QFIX SYSTEMS, LLC, Avondale, PA (US)

(72) Inventors: Daniel D. Coppens, Avondale, PA (US); John Damon Kirk, Ramsey, NJ (US)

(73) Assignee: QFIX SYSTEMS, LLC, Avondale, PA (US)

( * ) Notice: Subject to any disclaimer, the term of this patent is extended or adjusted under 35 U.S.C. 154(b) by 512 days.

(21) Appl. No.: 15/015,633

(22) PCT Filed: Aug. 8, 2014

(86) PCT No.: PCT/US2014/050335
§ 371 (c)(1),
(2) Date: Feb. 4, 2016

(87) PCT Pub. No.: WO2015/021377
PCT Pub. Date: Feb. 12, 2015

(65) Prior Publication Data
US 2016/0213337 A1 Jul. 28, 2016

Related U.S. Application Data

(60) Provisional application No. 61/950,459, filed on Mar. 10, 2014, provisional application No. 61/863,638, filed on Aug. 8, 2013.

(51) Int. Cl.
*A47C 27/08* (2006.01)
*A61F 5/01* (2006.01)
(Continued)

(52) U.S. Cl.
CPC .............. *A61B 6/04* (2013.01); *A61N 5/10* (2013.01); *A47C 27/086* (2013.01); *A61F 5/01* (2013.01); *A61N 2005/1097* (2013.01)

(58) Field of Classification Search
CPC .. A47G 9/10; A47C 7/38; A47C 7/383; A47C 27/08; A47C 27/086; A61F 5/01
(Continued)

(56) References Cited

U.S. PATENT DOCUMENTS 4,240,415 A * 12/1980 Wartman .............. A61L 15/12
528/359
4,483,333 A * 11/1984 Wartman .............. A61F 13/04
602/7
(Continued)

FOREIGN PATENT DOCUMENTS

CN 102421394 A 4/2012
EP 2 141 009 A1 1/2010
(Continued)

OTHER PUBLICATIONS

International Search Report for International Application No. PCT/US2014/050335 dated Jan. 14, 2015.
(Continued)

*Primary Examiner* — Robert G Santos
(74) *Attorney, Agent, or Firm* — RatnerPrestia

(57) ABSTRACT

A heat formable patient positioning cushion is provided including an impermeable or permeable outer shell; a filler material contained within an interior region defined by the outer shell; and a thermoplastic material applied to the outer shell, to the filler material, or to the outer shell and the filler material. The cushion has a first condition configured to be conformed to the anatomy of a patient in which the filler material moves relatively freely within the interior region defined by the outer shell, and a second condition conformed
(Continued)

to the anatomy of the patient in which the filler material is relatively fixed against movement within the interior region defined by the outer shell. Heating and cooling changes the cushion from the first condition to the second condition and reheating permits increased movement of the filler material as compared to the second condition to further conform the cushion to the anatomy of the patient.

26 Claims, 13 Drawing Sheets

(51) Int. Cl.
    *A61B 6/04*     (2006.01)
    *A61N 5/10*     (2006.01)

(58) Field of Classification Search
    USPC ........ 5/630, 636, 644, 654, 655.4, 690, 702, 5/911
    See application file for complete search history.

(56) References Cited

U.S. PATENT DOCUMENTS

| | | | | |
|---|---|---|---|---|
| 5,531,229 | A * | 7/1996 | Dean | A61B 90/16 128/845 |
| 5,794,628 | A * | 8/1998 | Dean | A61F 9/00 128/858 |
| 5,832,550 | A | 11/1998 | Hauger et al. | |
| 6,093,161 | A * | 7/2000 | Vlaeyen | A61F 5/05 602/21 |
| 6,138,302 | A * | 10/2000 | Sashin | A61B 6/0421 5/600 |
| 6,698,045 | B1 * | 3/2004 | Coppens | A61G 13/12 128/869 |
| 6,945,251 | B2 * | 9/2005 | Woodburn, III | A61B 6/0421 128/857 |
| 6,991,610 | B2 * | 1/2006 | Matsumoto | A61F 5/01 602/4 |
| 8,303,527 | B2 * | 11/2012 | Joseph | A61F 5/01 602/8 |
| 8,951,217 | B2 * | 2/2015 | Joseph | A61F 5/01 602/7 |
| 9,295,748 | B2 * | 3/2016 | Joseph | A61F 5/05825 |
| 9,561,128 | B2 * | 2/2017 | Joseph | A61F 5/01 |
| 9,655,761 | B2 * | 5/2017 | Joseph | A61F 5/028 |
| 9,757,265 | B2 * | 9/2017 | Joseph | A61F 5/01 |
| 2002/0108616 | A1 * | 8/2002 | Woodburn, III | A61B 6/0421 128/861 |
| 2002/0161319 | A1 * | 10/2002 | Matsumoto | A61F 5/01 602/8 |
| 2007/0004993 | A1 * | 1/2007 | Coppens | A61F 5/0104 602/7 |
| 2008/0319362 | A1 * | 12/2008 | Joseph | A61F 5/01 602/7 |
| 2012/0101417 | A1 | 4/2012 | Joseph | |
| 2012/0271007 | A1 | 10/2012 | Zhang | |
| 2013/0102940 | A1 * | 4/2013 | Joseph | A61F 5/01 602/7 |
| 2013/0300026 | A1 | 11/2013 | Zhang et al. | |
| 2014/0039366 | A1 * | 2/2014 | Joseph | A61F 5/05825 602/7 |
| 2014/0135672 | A1 * | 5/2014 | Joseph | A61F 5/028 602/19 |
| 2015/0238343 | A1 * | 8/2015 | Joseph | A61F 5/01 602/7 |
| 2016/0095739 | A1 * | 4/2016 | Coppens | A61B 90/16 128/845 |
| 2016/0206395 | A1 * | 7/2016 | Coppens | A61B 90/18 |
| 2016/0213337 | A1 * | 7/2016 | Coppens | A61N 5/10 |
| 2017/0189241 | A1 * | 7/2017 | Joseph | A61F 5/01 |
| 2018/0055671 | A1 * | 3/2018 | Joseph | A61F 5/01 |

FOREIGN PATENT DOCUMENTS

| | | |
|---|---|---|
| EP | 2 537 882 A1 | 12/2012 |
| WO | WO 2009/006925 A1 | 1/2009 |

OTHER PUBLICATIONS

Chinese Office Action for Chinese Application No. 201480055680.5, dated Mar. 5, 2018, including English translation, 13 pages.
Second Chinese Office Action for Chinese Application No. 201480055680.5, dated Oct. 10, 2018, including English translation—27 pages.
International Preliminary Report for International Application No. PCT/US2014/050335 dated Feb. 18, 2016.

* cited by examiner

HEAT FORMABLE PATIENT POSITIONING CUSHION, METHOD OF PRODUCING A HEAT FORMABLE PATIENT POSITIONING CUSHION, AND HEAT FORMABLE PATIENT POSITIONING SYSTEM

CROSS REFERENCE TO RELATED APPLICATION

This application is the U.S. national application of PCT Application No. PCT/US2014/050335, filed Aug. 8, 2014 which claims priority to Provisional Application No. 61/950,459, filed on Mar. 10, 2014, and Provisional Application No. 61/863,638, filed on Aug. 8, 2013, the disclosures of which are incorporated herein by reference in their entireties for all purposes.

BACKGROUND OF THE INVENTION

In radiotherapy it is important for the patient to be positioned in a way that is repeatable. The patient typically receives the total prescribed dose in a number of "fractions" spread over a number of weeks. It is critical that the patient be positioned accurately and repeatably for each of these fractions. This ensures that the dose is delivered to specified anatomy.

For this reason, there remains a need for improved supports or cushions for patient positioning. For example, it is desirable to have a custom formable cushion that is improved in terms of at least one of its performance, ease of use, ease of manufacturing, and cost.

SUMMARY OF THE INVENTION

A heat formable patient positioning cushion is provided including an impermeable or permeable outer shell; a filler material contained within an interior region defined by the outer shell; and a thermoplastic material applied to the outer shell, to the filler material, or to the outer shell and the filler material. In addition, the thermoplastic material can be discretely intermingled with the other filler materials. The cushion has a first condition configured to be conformed to the anatomy of a patient in which the filler material moves relatively freely within the interior region defined by the outer shell, and a second condition conformed to the anatomy of the patient in which the filler material is relatively fixed against movement within the interior region defined by the outer shell. Heating and cooling changes the cushion from the first condition to the second condition and reheating permits increased movement of the filler material as compared to the second condition to further conform the cushion to the anatomy of the patient.

The filler material may include discrete pieces, such as solid or hollow spheres; fibers; and/or a lofted felt. If it includes fibers, the fibers may be diced into pieces 0.5 mm to 10 mm in length.

The outer shell is optionally permeable to gas to facilitate heat transfer to the interior region of the outer shell, at least 20% of the surface area of the outer shell being formed from permeable material for example. Alternatively, the outer shell is optionally impermeable to facilitate at least one of a vacuum applied to the interior region of the outer shell and heating the cushion with a fluid. If the outer shell is impermeable to facilitate a vacuum, the cushion optionally includes a port positioned in the outer shell to apply the vacuum within the interior region of the outer shell. Such an outer shell can be impermeable to gas. The outer shell can be impermeable to water to facilitate heating the cushion with heated water.

The thermoplastic material of the cushion is optionally applied to the filler material as a coating or to an interior surface of the outer shell as a coating or a laminate. If a lofted felt is included in the cushion, it can be impregnated with the thermoplastic material. Also, such an impregnated lofted felt can be compressed such that, upon application of heat, the thermoplastic material melts and allows the lofted felt to expand.

Thermoplastic material can have a melting temperature of less than 200° F. It can include one or more of polycaprolactone, ethylene vinyl acetate (EVA) and wax.

A method of producing a heat formable patient positioning cushion is also provided, the cushion having a first condition configured to be conformed to the anatomy of a patient and a second condition conformed to the anatomy of the patient. The method includes mixing thermoplastic material with filler material; enclosing the mixture of thermoplastic material and filler material within an interior region of an outer shell such that heating and cooling changes the cushion from the first condition, in which the filler material moves relatively freely within the interior region of the outer shell, to the second condition, in which the filler material is relatively fixed against movement within the interior region of the outer shell, and such that reheating permits increased movement of the filler material as compared to the second condition to further conform the cushion to the anatomy of the patient.

The method can include mixing thermoplastic material with discrete pieces of filler material and/or mixing thermoplastic material with fibers of filler material. If fibers are used, the method can include dicing the fibers into pieces 0.5 mm to 10 mm in length.

The method can also include applying the thermoplastic material to the filler material as a coating or to an interior surface of the outer shell as a coating or a laminate.

The method optionally includes impregnating the thermoplastic material into a lofted felt material. If so, the method can also include heating and compressing the mixture into a thinned configuration such that, upon subsequent application of heat, the thermoplastic melts and allows the lofted felt material to expand.

A heat formable patient positioning cushion system is also provided such that it is configured to be used in conjunction with a support surface. The system includes a cushion having an impermeable or permeable outer shell, a filler material contained within an interior region defined by the outer shell, and a thermoplastic material applied to the outer shell, to the filler material, or to the outer shell and the filler material. An indexing feature is coupled to the cushion and positioned to locate the cushion with respect to the support surface. The indexing feature ensures that the cushion is placed in substantially the same position with respect to the support surface during each use and reducing movement of the cushion with respect to the support surface when in use.

The indexing feature of the system optionally includes at least one selected from the group consisting of a disk, a block, a rod, and a pin. Also, the support surface optionally includes a Silverman support or a patient support surface.

DETAILED DESCRIPTION OF THE INVENTION

Figure 1A:
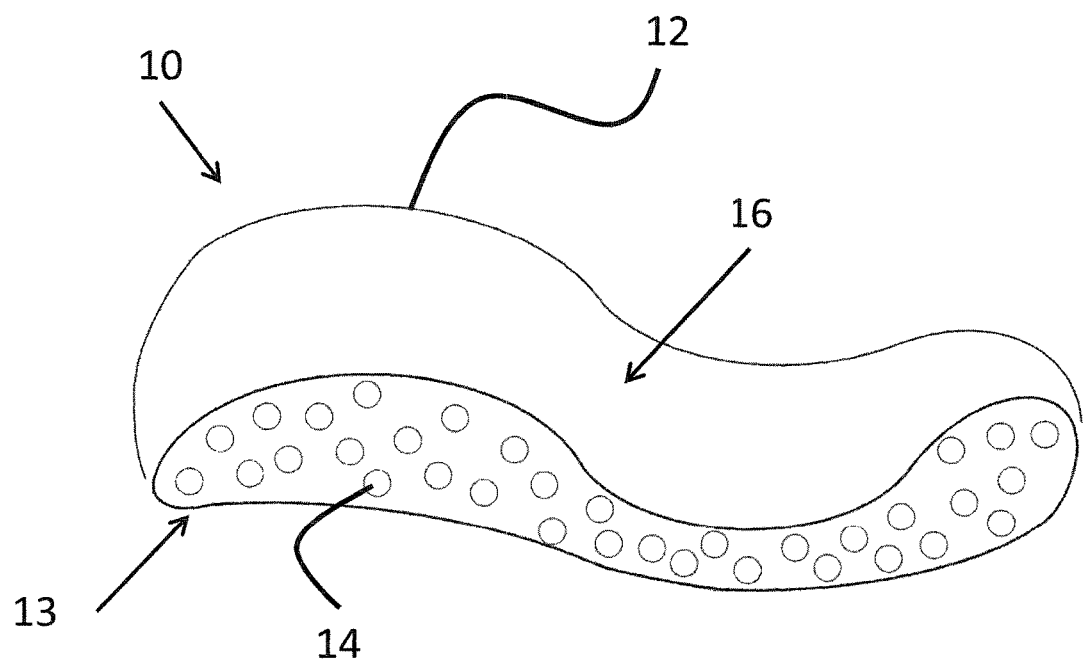
FIG. 1A shows a side view of an embodiment of a heat formable patient positioning cushion with an impermeable outer case in a first condition according to aspects of the invention.

Although the invention is illustrated and described herein with reference to specific embodiments, the invention is not intended to be limited to the details shown. Rather, various modifications may be made in the details within the scope and range of equivalents of the claims and without departing from the scope of the invention.

Foam cushions of high rigidity are beneficially used under a patient for positioning and comfort. Ideally, such cushions should be rigid and custom formable to the patient in order to be able to produce a cushion that is custom contoured to the patient's anatomy. Vacuum cushions, for example, may include an air impermeable coated fabric or film bag that is filled with polystyrene beads. The patient is placed on the cushion, which is soft when not under vacuum. The patient's anatomy sinks into the cushion, which forms to the contour of the patient. A vacuum is then pulled on the inside of the bag with a vacuum pump to draw the air out. When the air is evacuated, the cushion becomes rigid. These cushions are reusable, but in some cases they may tend to leak over a period of time.

Alternatively, a cushion can include polystyrene beads coated with a thermosetting polyurethane (PU) adhesive. This adhesive is activated by the presence of water. The user wets the cushion and then forms it to the patient's anatomy. The PU adhesive then sets irreversibly. The cushions must be packaged in a hermetically sealed foil bag. Since the presence of humidity in the air sets off the adhesive reaction, the product has a shelf life and if the packaging is punctured the cushion can harden immediately. In addition, the adhesive can give off a strong odor while curing, which can be unpleasant to a patient and potentially hazardous to a clinician who is exposed to this long term. Ideally, therefore, it is beneficial to have a cushion that does not present any unpleasant odors, has essentially infinite shelf life, and/or becomes rigid at room temperature after being formed to the patient's anatomy.

According to aspects of this invention, a preferred cushion is custom formable through the application of heat. The heat source melts a thermoplastic polymer which allows the low density cushion material to be formed to the contour of the patient. When cooled back to room temperature, it becomes a rigid cushion contoured to the unique anatomy of the individual patient. With the reapplication of heat, it can also be reformed for a subsequent patient or locally modified. It can be used for radiation therapy or any other patient positioning applications such as diagnostic imaging.

Referring to the figures generally, this invention provides cushions, such as cushions 10, 20, 30, 85, 90, 102, and 116, used for patient positioning and formable by heat. The cushion includes an outer shell, such as outer shells 12, 22, 32, and 92, that may be permeable or impermeable. The outer shell defines an interior region, such as interior regions 13, 23, 33, and 93, containing filler material, such as filler material 14, 24, 34, 40, 72, 84, and 94. A thermoplastic material, such as thermoplastic material 42, is applied to either the outer shell or the filler material, or both the outer shell and filler material.

The filler material, such as filler material 14, 24, 34, 40, 72, 84, and 94, may include fibers, such as fibers 72, and/or a lofted felt such as lofted felt 84. The fibers may be coated with a thermoplastic material. The lofted felt may be impregnated with thermoplastic material. The impregnated lofted felt may be compressed such that, upon application of heat, the thermoplastic material melts and allows the lofted felt to expand.

The cushion has a first condition, such as shown in FIGS. 1A, 2, 3A, and 9A, to be conformed to the anatomy of a patient in which the filler material moves relatively freely within the interior region. The cushion also has a second condition, such as shown in FIGS. 1B, 3B, and 8C, that is conformed to the anatomy of the patient in which the filler material is relatively fixed against movement within the interior region. The cushion is adapted such that heating and then cooling of the cushion changes the cushion from the first condition to the second condition. Reheating the cushion in the second condition permits limited movement of the filler material contained in the interior region to further conform the cushion to the anatomy of the patient. The limited movement permitted by reheating is an increased degree of movement as compared to the relatively fixed state of the filler material in the second condition.

The filler material may include discrete pieces, such as solid or hollow spheres such as spherical filler 40; fibers such as fibers 72; and/or a lofted felt such as lofted felt 84. If it includes fibers, the fibers may be diced into pieces 0.5 mm to 10 mm in length. Also, the outer shell 12, 22, 32, or 92 is optionally permeable to gas to facilitate heat transfer to the interior region of the outer shell, at least 20% of the surface area of the outer shell being formed from permeable material for example. Alternatively, the outer shell 12, 22, 32, or 92 is optionally impermeable to facilitate at least one of a vacuum applied to the interior region of the outer shell and heating the cushion with a fluid. If the outer shell is impermeable to facilitate a vacuum, the cushion optionally includes a port 28 positioned in the outer shell to apply the vacuum within the interior region of the outer shell. Such an outer shell 12, 22, 32, or 92 can also be impermeable to gas. The outer shell can be impermeable to water to facilitate heating the cushion with heated water.

Figure 4:
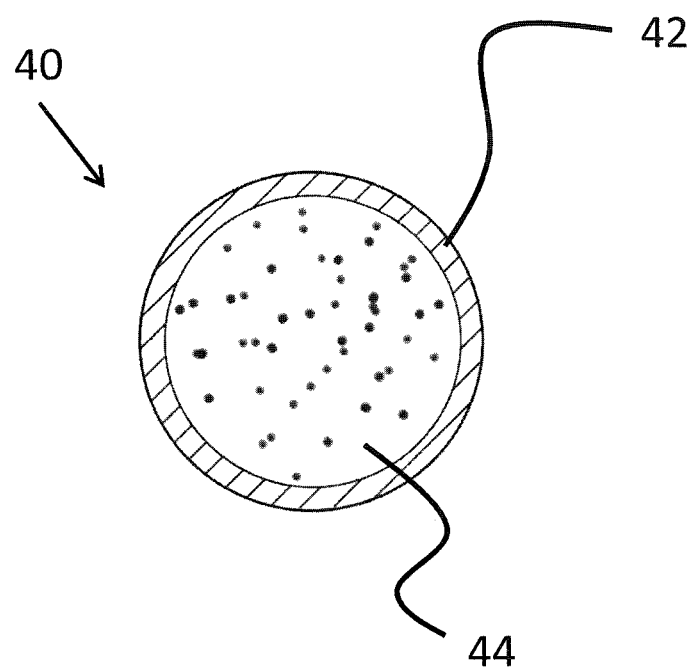
FIG. 4 is an illustration of an embodiment of a discrete piece of filler material according to aspects of the invention.
Figure 7:
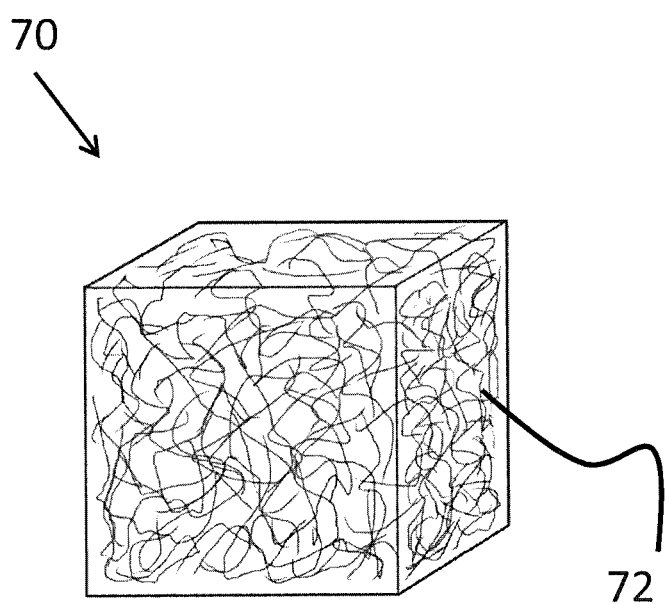
FIG. 7 depicts an embodiment of filler material made of lofted felt materials in accordance with aspects of the invention.
Figure 8A:
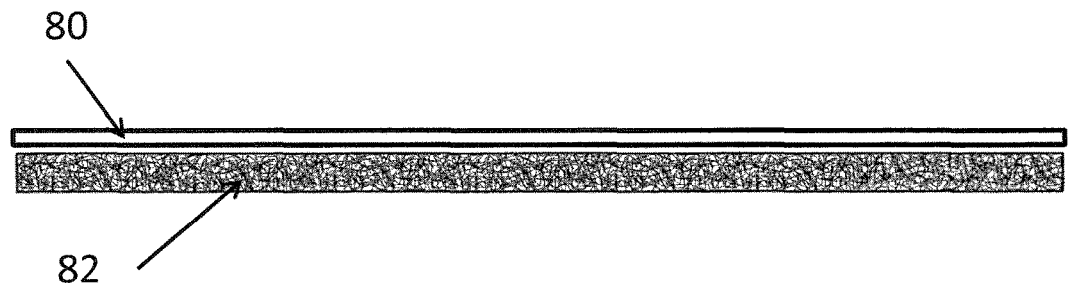
FIG. 8A depicts an embodiment of a compressed thermoplastic material laminated over felt material in accordance with aspects of the invention.
Figure 8B:
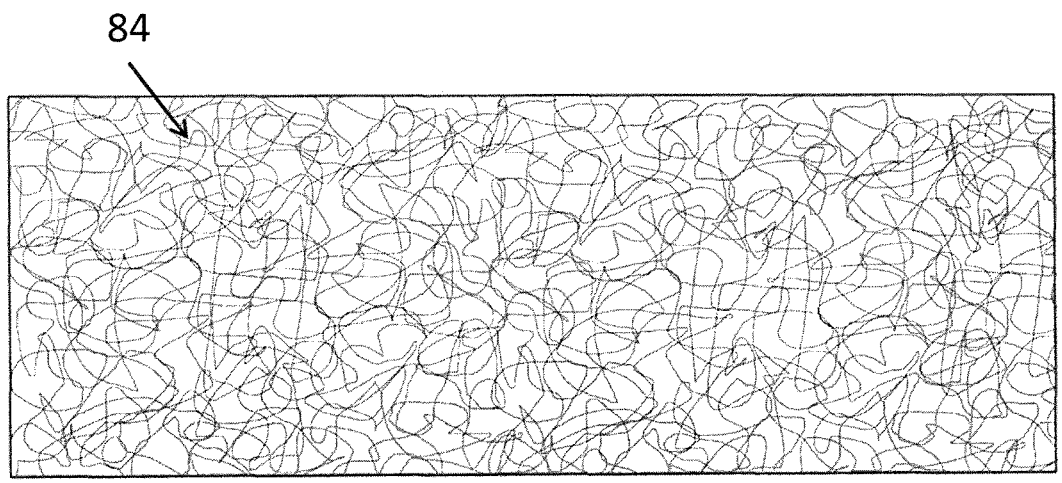
FIG. 8B depicts an embodiment of a lofted felt material according to aspects of the invention.
Figure 8C:
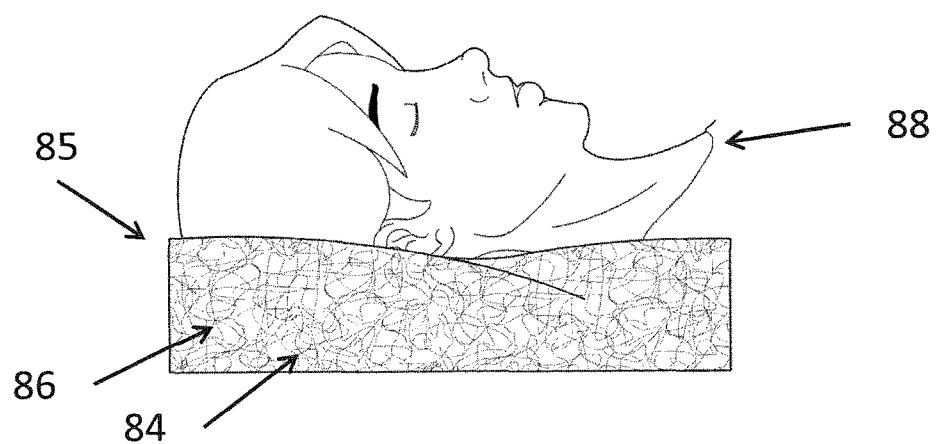
FIG. 8C depicts an embodiment of a cushion made of a lofted felt material in accordance with aspects of the invention.
Figure 9A:
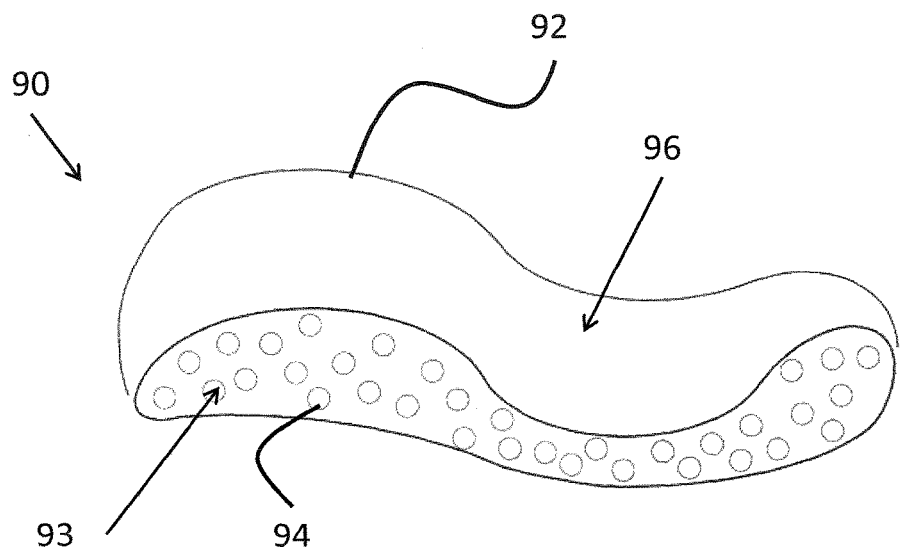
FIG. 9A shows a preferred embodiment of an outer case construction employing a low temperature thermoplastic coating on an interior of the outer case according to aspects of the invention.
Figure 9B:
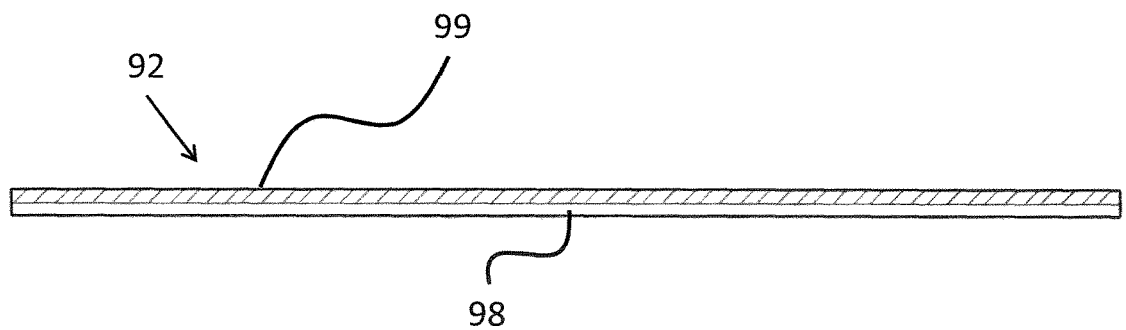
FIG. 9B shows a side view of an embodiment of a heat formable patient positioning cushion including a PCL coated outer case according to aspects of the invention.

The thermoplastic material of the cushion is optionally applied to the filler material as a coating (such as illustrated in FIG. 4) or to an interior surface of the outer shell as a coating or a laminate (such as illustrated in FIG. 9B). If a lofted felt such as shown in FIGS. 7-8C is included in the cushion, it can be impregnated with the thermoplastic material. Also, such an impregnated lofted felt can be compressed such that, upon application of heat, the thermoplastic material melts and allows the lofted felt to expand. Thermoplastic material can have a melting temperature of less than 200° F. It can include one or more of polycaprolactone (PCL), ethylene vinyl acetate (EVA) and wax, for example, but equivalent materials are contemplated as well.

Figure 1B:
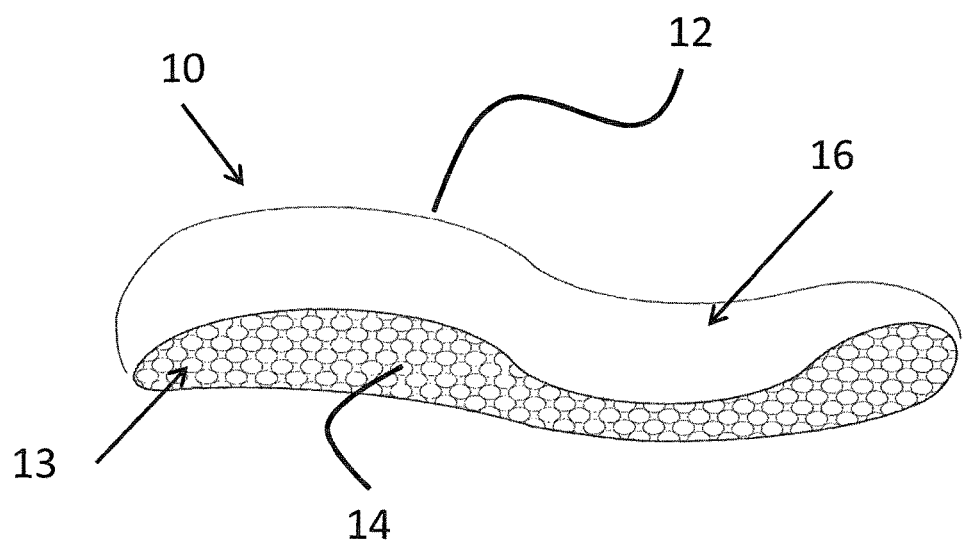
FIG. 1B shows a side view of the heat formable patient positioning cushion shown in FIG. 1A in a second condition according to aspects of the invention.

Referring specifically to FIGS. 1A and 1B, an embodiment of a cushion is having an outer casing/outer shell filled with discrete pieces of coated filler material to be heat formable to the anatomy of a patient for patient positioning is shown. The cushion 10 includes an outer shell 12, an interior region 13 defined by the outer shell 12, and filler material 14 contained in the interior region 13. The cushion 10 has a first condition, as shown in FIG. 1A, to be conformed to the anatomy of a patient and may be heated and cooled to a second condition, as shown in FIG. 1B, in which the cushion 10 is conformed to the anatomy of the patient.

The surface area 16 of the outer shell 12 may be constructed of a material such that the outer shelf 12 is generally impermeable, keeping air within the interior region 13 and preventing external air, gases, and liquids from penetrating the outer shell 12 into the interior region 13. In one embodiment, the surface area 16 of the outer shell 12 is impermeable to liquid or gas permitting the cushion 10 to be heated by exposure to a liquid (e.g., a hot water bath) or gas (e.g., an oven) such that the liquid or gas does not penetrate the outer shell 12 into the interior region 13.

Figure 2:
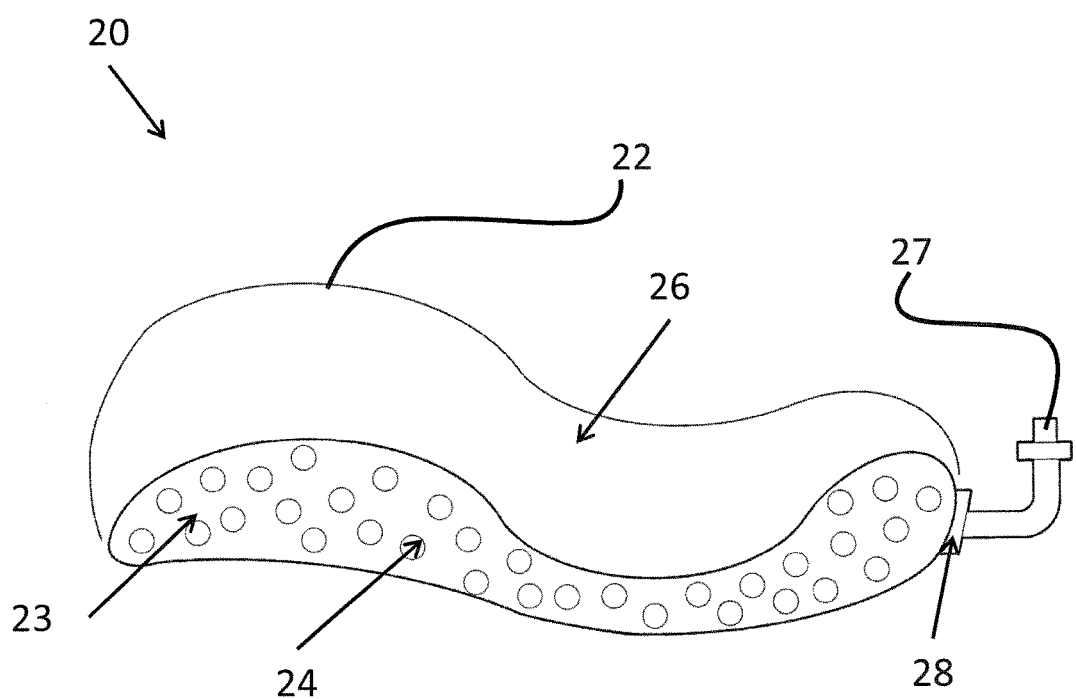
FIG. 2 shows a side view of an embodiment of a heat formable patient positioning cushion that includes a vacuum valve to remove air from inside the outer case in accordance with aspects of the invention.

In an embodiment as depicted in FIG. 2, a cushion 20 includes an outer shell 22, an interior region 23 defined by the outer shell 22, and filler material 24 contained within the interior region 23. The outer shell 22 includes a surface area 26 that is generally impermeable such that air and gas remains within the interior region 23. As the cushion 20 is heated and cooled, thus changed from the first condition to the second condition, excess air remains in the interior region 23 due to the impermeable surface area 26 of the outer shell 22. A vacuum valve 27 may be attached to a port 28 formed on the outer shell 22 to remove excess air in the interior region 23 during or after the cushion 20 has changed to the second condition. By removing the excess air, the rigidity of the cushion 20 may be increased, thereby increasing the effectiveness of the cushion in immobilizing the anatomy of a patient.

If an impermeable outer shell 22 is used, the cushion is optionally formed to the patient's anatomy without heating. More specifically, the vacuum can be applied in order to evacuate air from the interior region 23 to hold the filler material in a rigid configuration even without the application of heat. Therefore, a user of cushion 20 has the option of heat-forming or vacuum-forming the cushion, depending on the user's preference, the preference of the patient, or the equipment available to the user to heat the cushion (for example a water bath or oven) or to apply vacuum to the cushion (for example a vacuum source or pump).

Figure 3A:
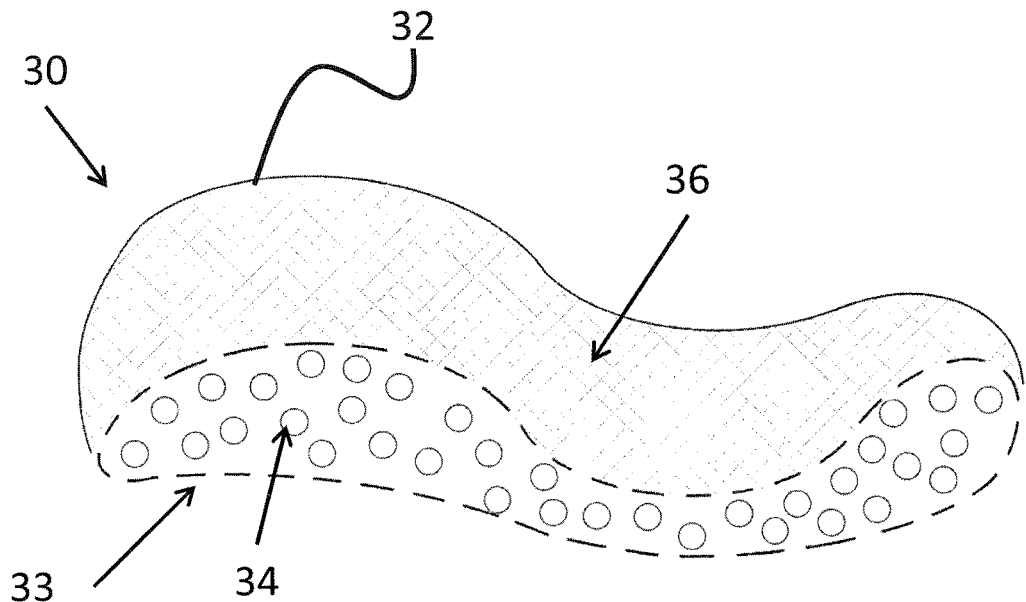
FIG. 3A shows a side view of an embodiment of a heat formable patient positioning cushion with a permeable outer case in a first condition in accordance with aspects of the invention.
Figure 3B:
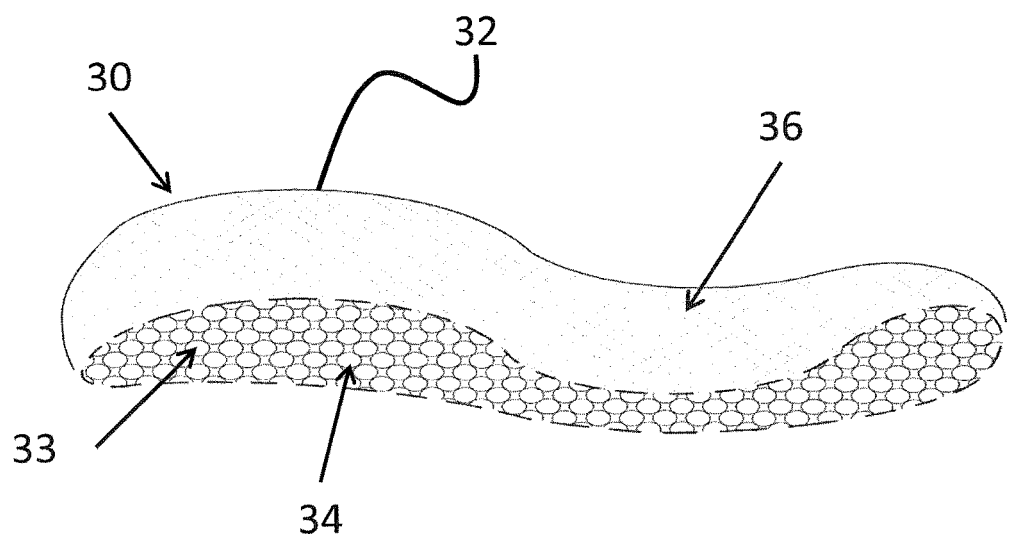
FIG. 3B shows a side view of the heat formable patient positioning cushion shown in FIG. 3A in a second condition in accordance with aspects of the invention.

Referring next to FIGS. 3A and 3B, an alternative embodiment of a cushion to be heat formable to the anatomy of a patient for patient positioning is shown according to aspects of the invention. The cushion 30 includes an outer shell 32, an interior region 33 defined by the outer shell 32, and filler material 34 contained within the interior region 33. The cushion 30 functions similarly to cushions 10 and 20 in that cushion 30 has a corresponding first condition and second condition. The cushion 30 has a first condition, as shown in FIG. 3A, to be conformed to the anatomy of a patient and may be heated and cooled to a second condition, as shown in FIG. 3B, in which the cushion 10 is conformed to the anatomy of the patient. The outer shell 32 may be constructed of a material such that the surface area 36 of the outer shell 32 is generally permeable, permitting air and gas to penetrate the outer shell 32 into the interior region 33.

In an embodiment, the surface area 36 is permeable to gas to facilitate heat transfer to the interior region 33 of the outer shell 32. More specifically, the outer shell 32 is permeable to gas in order to facilitate the transfer of heat to the interior region 33 of the outer shell 32. Such permeability helps to encourage uniformity of heat transfer, accelerates heating, and permits the flow of heated gas into and out of the interior region 33.

The cushions 10, 20, and 30 as described herein are exemplary and not exclusive. It is contemplated that many combinations of the features described in association with cushions 10, 20, and 30 may be utilized in accordance with the invention, and features of those embodiments can be combined in various ways and permutations in order to form cushions that enjoy the various benefits of those features.

The surface area of the outer shell may be partially permeable and partially impermeable. In one embodiment, the surface area is at least about 20% permeable to gas to facilitate heat transfer to the interior region of the outer shell. The remainder of the outer shell may be relatively or completely impermeable so as to control the infiltration of gas into or out from the interior region of the shell.

In one embodiment, the surface area of the outer shell includes permeable sections and impermeable sections. The sections of material may be selected for patient comfort and/or for cushion performance and forming. The cushions may, for example, include a vacuum valve attached to a port formed in the outer shell which has a permeable and/or impermeable surface area to remove excess air from the interior region during or after the time when the cushion is changed to the second condition. In an embodiment, a vacuum valve is attached to one or more impermeable sections of the cushion. In such an embodiment, the section or sections to which the vacuum valve is attached may be isolated from other permeable and/or impermeable sections of the cushion. Other suitable cushion formations will be understood by one of skill in the art from the description herein.

The filler material, such as filler material 14, 24, and 34, will now be described with reference to FIGS. 4-6. FIG. 4 shows a piece of filler material coated with a thin coating of low melting temperature thermoplastic. The filler material may comprise discrete pieces such as discrete piece 40. The discrete pieces of filler material can be any shape including but not limited to; spherical (solid or hollow), conical, pyramidal, conical, and cubic, or any combination thereof. The casing/outer shell may be permeable or impermeable to fluids. The casing (e.g., outer shells 12, 22, and 32) contains the discrete pieces 40 of filler material so that they do not come out. The discrete pieces 40 may be foam polymer pieces of filler material and may be produced from a polystyrene material 44 coated in a thin coating of material, such as a thermoplastic material, that can bond adjacent particles together under application of heat. For example, a thermoplastic material such as Polycaprolactone (PCL) 42 or other suitable material that can bond under application of heat can be used. The filler material may be coated with a thermoplastic casing/outer shell, impregnated with filler, and/or mixed with thermoplastic powders, thermoplastic pellets, thermoplastic nanoparticles, etc. In an embodiment, the discrete pieces are pieces of thermoplastic material without filler material. Other suitable shapes, configurations, and materials for the thermoplastics and filler materials will be understood by one of skill in the art from the description herein.

Figure 5:
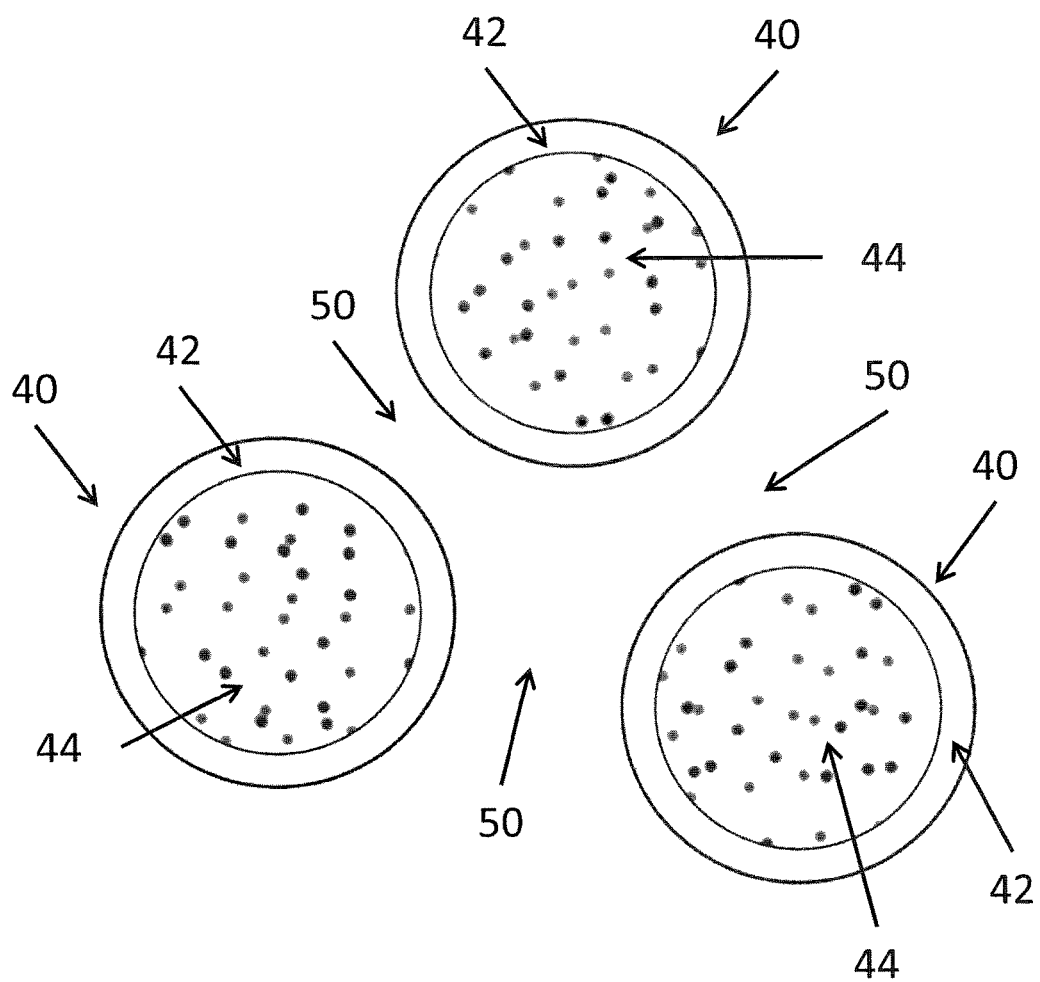
FIG. 5 is an illustration showing the discrete pieces of filler material of FIG. 4 in a first condition of the heat formable cushion in accordance with aspects of the invention.

FIG. 5 shows discrete pieces of filler material coated with a low melting temperature thermoplastic. These pieces of filler are in the state prior to being heated and are free to move with respect to each other. These discrete pieces 40 of filler material are initially rigid and move relatively freely (e.g., free flowing) within the interior region of the outer shell at about room temperature and/or temperatures below the melting or softening point of the materials that form the discrete pieces 40. The coating 42 is hard and the pieces 40 of filler material do not stick to each other at about room temperature and/or temperatures below the melting point of the components that form the discrete pieces 40, allowing the pieces 40 to be separated as depicted by spaces 50 between them.

Figure 6:
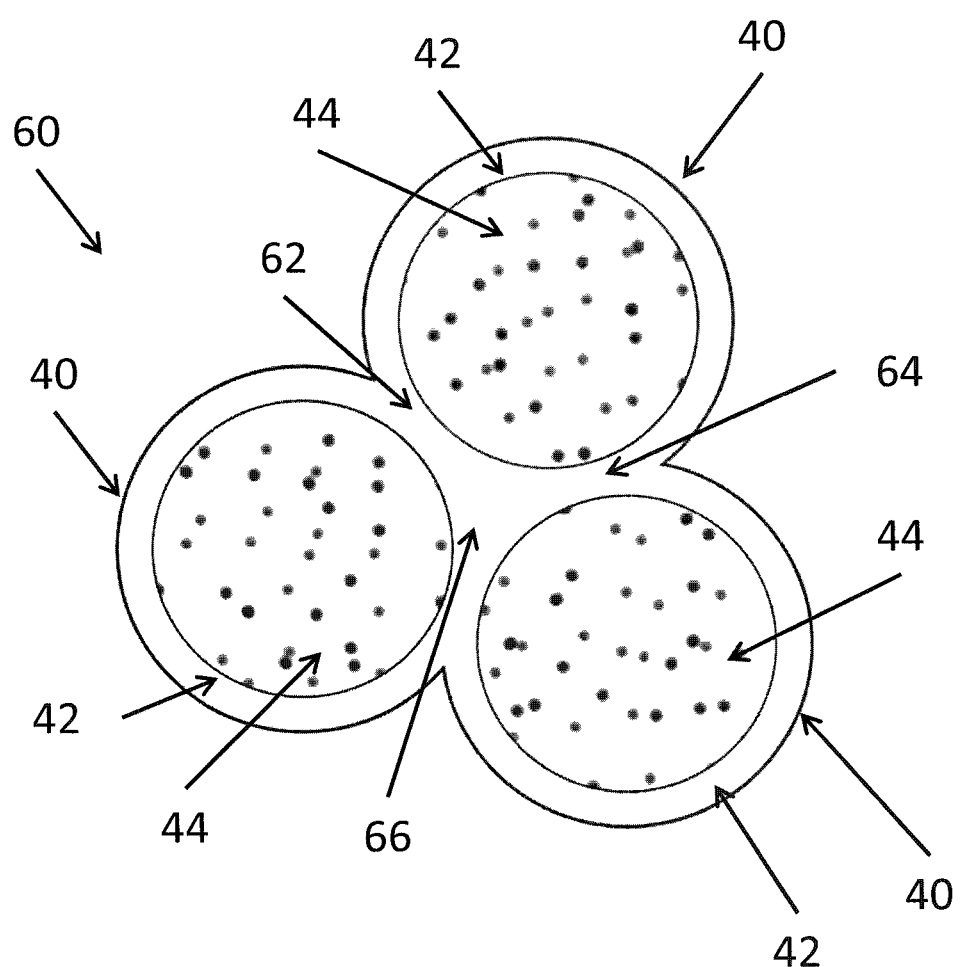
FIG. 6 is an illustration showing the discrete pieces of filler material of FIG. 4 in a second condition of the heat formable cushion according to aspects of the invention.

FIG. 6 shows discrete pieces of filler material coated with a low melting temperature thermoplastic. These pieces of filler material are in the state after being heated and subsequently cooled to room temperature. The coatings of low melting temperature thermoplastic have fused and locked the pieces of filler material together. When heated above the melting temperature (e.g., the melting point of PCL), the materials used to form the discrete pieces 40 and/or the surface coating 42 softens or becomes molten. Heat may be applied using either a hot water bath or a convection oven, depending on whether the outer shell includes permeable or impermeable surface areas and depending on the equipment available to the user of the cushion. Other suitable heating applications will be understood by one of skill in the art from the description herein. The cushion (e.g., cushions 10, 20, and 20) is then formed to the contour of the anatomy of a patient (e.g., changed from the first condition to the second condition of the cushion as described above as the cushion cools and the coating 42 cools). When the discrete pieces 40 with the PCL or other thermoplastic material coating 42 cool back below the thermoplastic materials' respective melt temperature, the pieces 40 of filler material stick together, as depicted by sticking spots 62, 64, and 66 in FIG. 6, forming a rigid foam cushion.

Polystyrene beads/discrete pieces 40 (or other polymer) may be coated with PCL. It is desirable to coat the beads in such a way that an individual sphere of polymer foam is coated by a thin coating of PCL. At room temperature, initially, they to do not stick to each other, making the cushion pliable/formable. Once heated, the PCL softens, causing the beads to stick together but remain pliable/formable. The interior region of the cushion filled with these beads is then formed around the anatomy of a patient for patient positioning (such as around the back of the patient's head). Once the PCL cools, the beads stick together (such as is depicted in FIG. 6), solidifying and is creating a custom form. If this bead/PCL combination is packaged inside of a fabric shell or bag, the resulting cushion can be used to position a patient's head and/or other portions of the patient's anatomy for radiotherapy treatment.

Thus, when the cushion is at the first condition, the discrete pieces 40 may move relatively freely within the interior space formed by the outer shell, as depicted in FIG. 5. When the cushion is heated to the melting point of the material from which the filler material and/or the coatings 42 are made, the discrete pieces 40, or at least the coatings 42 of the discrete pieces 40, melt together. While heated, the cushion can be formed to the anatomy of a patient, causing the discrete pieces 40 to be relatively fixed against motion (FIG. 6) with respect to each other as opposed to moving relatively freely (FIG. 5) with respect to each other. As the cushion cools below the melting temperature of the filler material and/or the coatings 42, the filler material as melted together hardens, thereby changing the cushion from the first condition to the second condition.

In addition, the cushion can be reformed using a hot air gun or other heat source to improve the contour or to modify the contour to adapt to changing requirements during the course of radiation therapy treatment. The cushion in the second condition may be reheated to permit limited movement of the filler material that was previously relatively fixed against motion as depicted in FIG. 6. For example, reheating permits increased movement of the filler material as compared to the second condition to further conform the cushion to the anatomy of the patient. The relatively increased movement of the filler material in the reheating process allows the cushion in the second condition to be modified after the cushion has changed from the first condition to the second condition. This permits adjustment of the shape of the cushion for a particular patient, modification of the cushion to facilitate repositioning of the patient in subsequent treatments, or reuse of the cushion for subsequent patients.

The discrete pieces 40 of filler material, as well as material 44 and coating 42 may be formed of various thermoplastics other than PCL. In an embodiment, such thermoplastics have a lower melting temperature than PCL, allowing the cushion to be heated to a lower temperature before use for forming to the anatomy of a patient. Advantageously, such thermoplastics reduce the time required to reach the melting temperature, thereby improving working time. In an embodiment, the thermoplastics have a melting temperature of less than about 200 F. Such thermoplastics may include ethylene vinyl acetate (EVA) and/or wax. In an embodiment, the thermoplastics used are paraffin wax, which advantageously can be tuned and optimized to provide a desired working time of the cushion. The melting point of paraffin wax is about 100 F, such that the cushion can be formed at a relatively low temperature compared to, for example, when PCL is used. The pieces 40 of filler material can also consist of hollow polymer spheres or microspheres coated with the low temperature polymer. This may be done to lower the attenuation of the cushion and may be incorporated to improve treatment in modalities such as Proton Therapy.

Referring to FIGS. 7-8C, a lofted felt impregnated with PCL is shown. The filler material 70 may be formed of fibers and/or lofted felt materials 72. It is also possible to impregnate lofted felt materials 72 with PCL and/or other thermoplastic materials described above. This can be accomplished by impregnating the felt through traditional laminating or coating processes utilizing thermoplastic materials. In an embodiment as depicted in FIG. 8A, the thermoplastic material is compressed and heated, leading to a thin configuration 80, and is laminated over the felt material 82. When heated, the thermoplastic melts, allowing the felt to loft again as depicted in FIG. 8B, leaving the felt fibers 84 coated with a thin layer of thermoplastic. When the material is heated, it expands (lofts) such that the total density of the material 84 is very low. The preferred polymer is PCL. This felt can then be diced into small pieces of 0.5 mm to 10 mm in size so that they flow freely prior to forming. In one embodiment, the felt is diced into portions or squares. The diced felt may be contained within the interior region of the cushion. It is contemplated that a combination of diced felt and discrete pieces 40 may be contained within the interior region of the cushion.

When using a lofted felt material as the filler material, it is possible to preform the cushion 85 into various shapes and configurations. For example, the lofted felt, impregnated with a plastic material for bonding, can be compressed into a board-like configuration or other pre-formed shape, as depicted in FIG. 8C. In such a configuration, the impregnated and compressed felt or fibrous material can then be cut into shapes or otherwise formed for use in the cushion. For example, it can be formed into particular shapes by stamping, mechanical cutting or heat cutting, or any other known manufacturing technique to form smaller pieces from larger boards or shapes of compressed fibrous materials. The various configurations of the compressed felt or fibrous material may be used in a heat formable cushion 85 to conform to the anatomy of a patient 88.

Such a formation method may have substantial advantages with respect to the storage, packaging, shipment, and/or handling of the pre-formed cushions or the interior components thereof. For example, flattened and compressed fibrous filler material can be stacked or tightly packaged within a container for shipment, storage, or inventory. This can reduce shipment costs and package volume. Also, the cutting of smaller shapes from larger pieces of compressed fibrous material can reduce waste during manufacturing.

In use, the compressed fibrous material of the cushion will expand and the fibers will separate from one another upon the application of heat. More specifically, the softening or melting of the bonding material will allow the fibers to separate from one another and thereby expand to conform to the patient's anatomy. In essence, the previously compressed fibrous material will "plump" as heat is applied as the fibers relax with respect to one another. By selecting the fibrous material, the plastic coating or bonding material, the degree of compression in manufacturing, and other aspects of the manufacturing process, the ratio of the height of the fibrous material before and after the application of heat can be adjusted.

It is contemplated that the compressing and expanding properties of such lofted felt materials may be obtained using other materials, such as open or closed cell foams. Open cell foams, for example, are advantageous as such foams are substantially transparent to radiation used for treatment of a patient (e.g., X-rays, etc.) in accordance with the invention. In one embodiment, an open cell foam (e.g., cellulose, conventional sponge materials, etc.) is exposed to or filled with a thermoplastic (e.g., thermoplastic powder, thermoplastic nanoparticles, etc.) that substantially or at least partially coats the cell walls of the open cell foam. The open cell foam with the thermoplastic coating on the cell walls may then be optionally heated and compressed, causing the thermoplastic to melt. The compression forms the open cell foam into a generally flat structure, which is advantageous in reducing space needed for shipment of the open cell foam and/or storage of the open cell foam. The open cell foam may then be heated from the compressing form, causing the foam to expand, in a manner similar to the lofted materials as described with respect to FIGS. 7-8C. After the foam expands and prior to cooling, the foam may be used as a formable cushion or part of a formable cushion to be shaped to correspond to the anatomy of a patient, similar to cushions 10, 20, 30, 85, 90, 102 and 116. Alternatively, the open cell foam may be impregnated with thermoplastic pellets, thermoplastic nanoparticles, etc.

Referring next to FIGS. 9A and 9B, an embodiment of a cushion according to aspects of the invention is shown. The cushion 90 includes an outer shell 92, an interior surface 93 defined by the outer shell 92, and filler material 94 contained within the interior surface 93. The outer shell 92 has a surface area 96 that may be permeable or impermeable substantially as described with respect to cushions 10, 20, and 30. The filler material 94 may be of a form and material (e.g., discrete pieces 50, impregnated lofted felt 72, 84, etc.) as described above. The outer shell 92 may include a coated layer, as depicted in the cross-sectional view of FIG. 9B. In an embodiment, the exterior surface 99 is a fabric material and the interior surface 98 is coated with thermoplastic material such as PCL, EVA, wax, etc.

Because the thermoplastic material (e.g., PCL, EVA, wax, paraffin wax, etc. as described above) is on the interior surface 98 of this cushion 90 as opposed to inside on the filler material 94, it heats up faster, and becomes formable more quickly, than the embodiment with a thermoplastic coating (e.g., PCL, EVA, wax, paraffin wax, etc. as described above) on some or all of the filler material. Thus, the cushion 90 may be changed from the first condition to the second condition faster in such embodiments.

All materials used and described herein are preferably selected to be radiolucent and of low density to maximize their compatibility with diagnostic imaging and treatment modalities. These include but are not limited to CT, PET/CT, SPECT, MRI, Radiation Therapy, MV x-rays, Proton and other particle therapies, brachytherapy, image guided radiosurgery.

Figure 10:
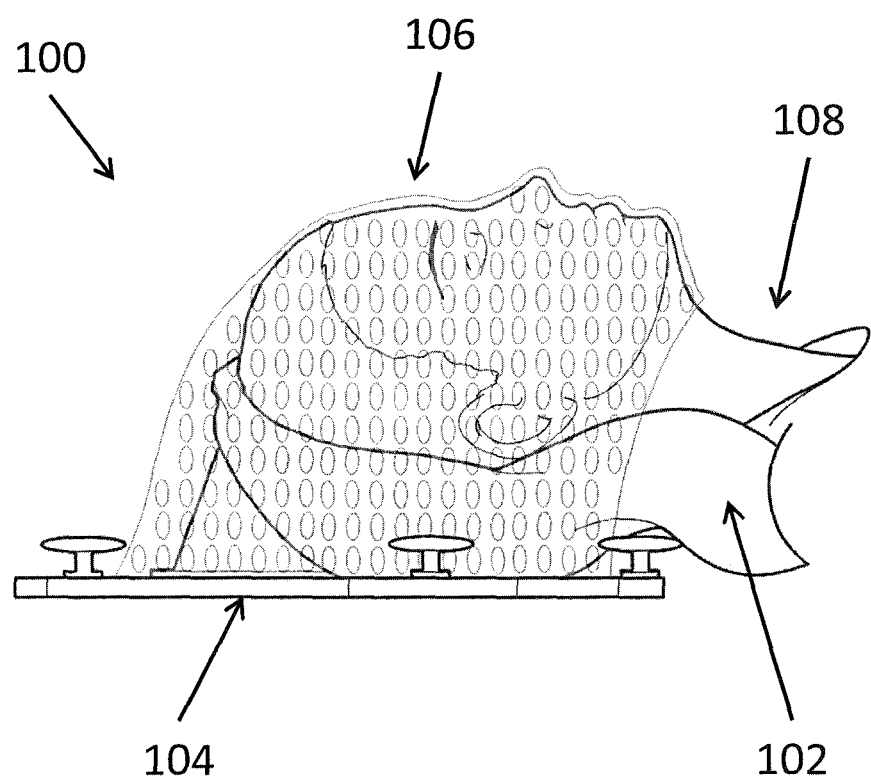
FIG. 10 shows a formable patient positioning cushion in use with a support structure to form a heat formable patient positioning cushion system in accordance with aspects of the invention.
Figure 11:
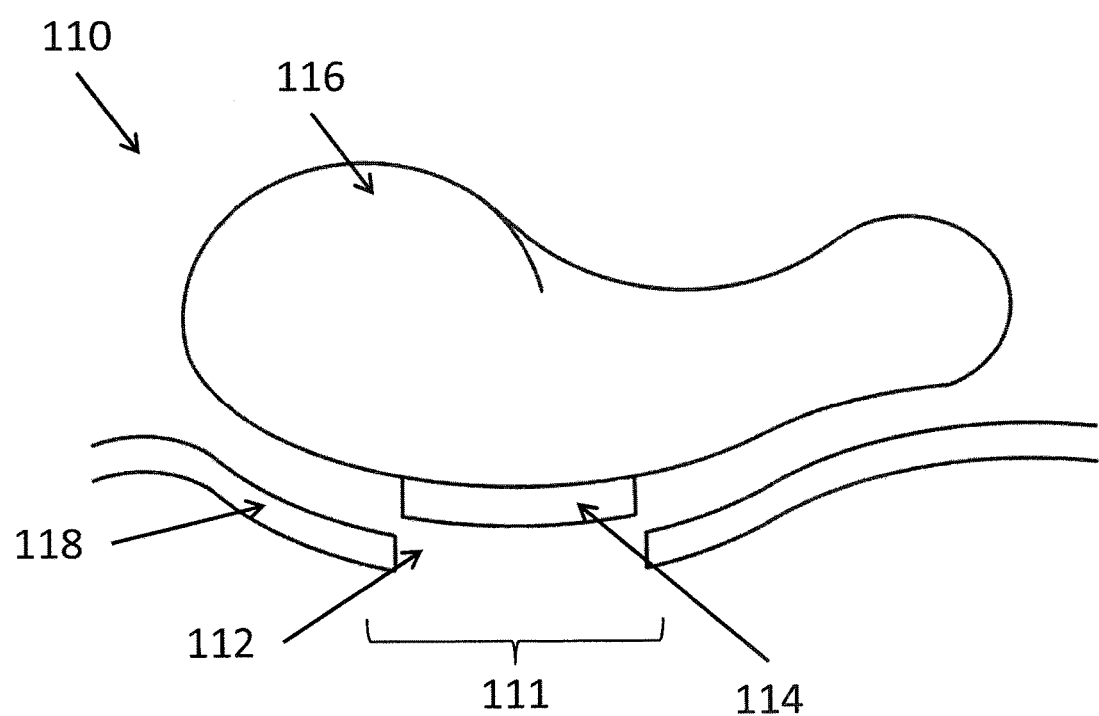
FIG. 11 shows an embodiment of a formable patient positioning cushion with a support structure that utilizes an indexing feature according to aspects of the invention.

A heat formable patient positioning cushion system is also provided such that it is configured to be used in conjunction with a support surface. Referring generally to FIGS. 10 and 11, the system 100 includes a cushion 102 having an impermeable or permeable outer shell, a filler material contained within an interior region defined by the outer shell, and a thermoplastic material applied to the outer shell, to the filler material, or to the outer shell and the filler material. An indexing feature 111 is coupled to the cushion 102, 116 and positioned to locate the cushion 102, 116 with respect to the support surface 104, 118. The indexing feature 111 ensures that the cushion 102, 116 is placed in substantially the same position with respect to the support surface 104, 118 during each use and reducing movement of the cushion 102, 116 with respect to the support surface 104, 118 when in use.

The indexing feature 111 of the system optionally includes at least one selected from the group consisting of a disk, a block, a rod, and a pin. Also, the support surface 104, 116 optionally includes a Silverman support or a patient support surface. The indexing feature 111 may also include a recess 112 in the support structure 118 configured to interface with a disk (e.g., disk 114), a block, a rod, a pin, etc., on the cushion 116. Alternatively, the indexing feature may include a recess in the cushion 116 configured to interface with a disk, a block, a rod, a pin, etc., on the support structure 118.

Referring to FIG. 10, an embodiment of a cushion used in a patient positioning system is shown. The patient positioning system 100 includes a cushion 102 formed to the anatomy of a patient 108, a support surface 104, and a thermoplastic member 106 formed over the anatomy of the patient 106. The thermoplastic member 106 may be a preform member as described in U.S. patent application Ser. No. 14/134,685, which is incorporated herein by reference.

The cushion 102 is in the second condition and has been formed to the anatomy of the patient 108. The cushion 102 rests against the support structure 104 to aid in positioning the patient 108 for treatment (e.g., radiotherapy treatment, etc.). The support structure 104 may include a Silverman support and/or a patient support surface.

In an embodiment as depicted in FIG. 11, the patient positioning system 110 includes an indexing feature 111 that can be used to improve immobilization of the patient by ensuring the cushion 116 is placed in the same location each time the patient is treated and by preventing the cushion 116 from moving during treatment. The indexing feature 111 may include a rod, a disk, a block, a pin and/or other suitable indexing features that will function in accordance with the invention as will be understood by one of skill in the art from the description herein. The indexing feature 111 may be positioned on the cushion 116, the support surface 118, or both. It is contemplated that more than one indexing feature and several types of indexing features may be utilized to effectuate the present invention.

Figure 12:
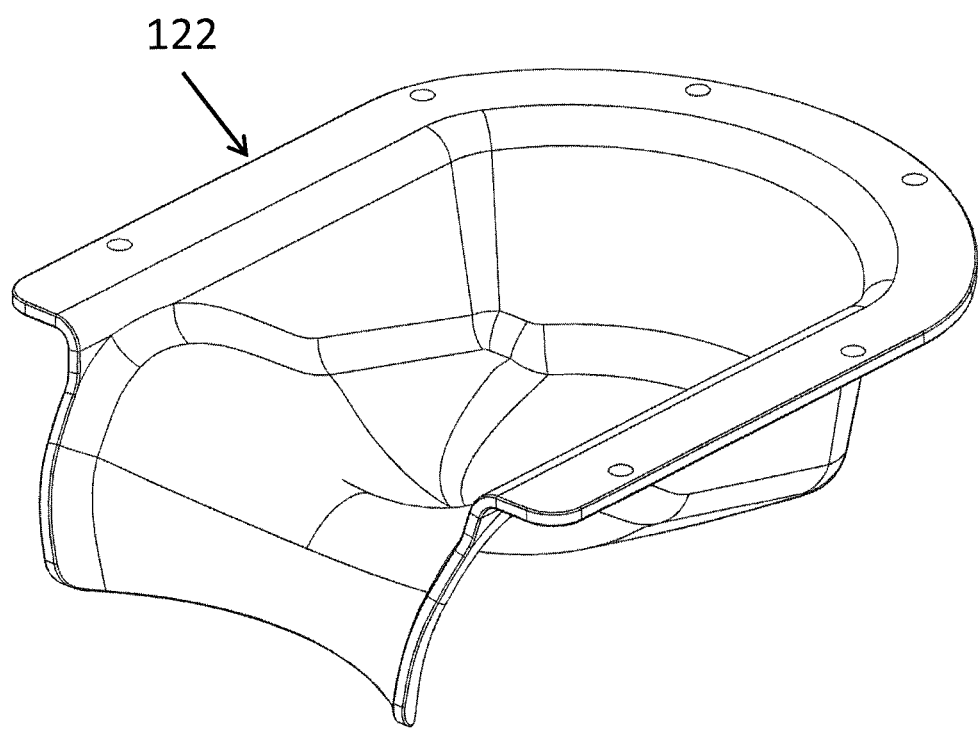
FIG. 12 is an isometric view of a cushion retaining device according to aspects of the invention.

Referring next to FIG. 12, a cushion retaining device is shown. The cushion retaining device 122 may be utilized in system 100 as the support surface 104. The cushion retaining device 122 may be provided to both locate a cushion (e.g., cushions 10, 20, 30, 85, 90, 102 and 116) and to increase the cushion's resistance to patient movement. In one embodiment, the cushion retaining device 122 is indexed to either the patient support surface (e.g., support surface 104) and/or to a secondary structure (e.g., structure 132 of FIG. 13) attached to the patient support surface.

Figure 13:
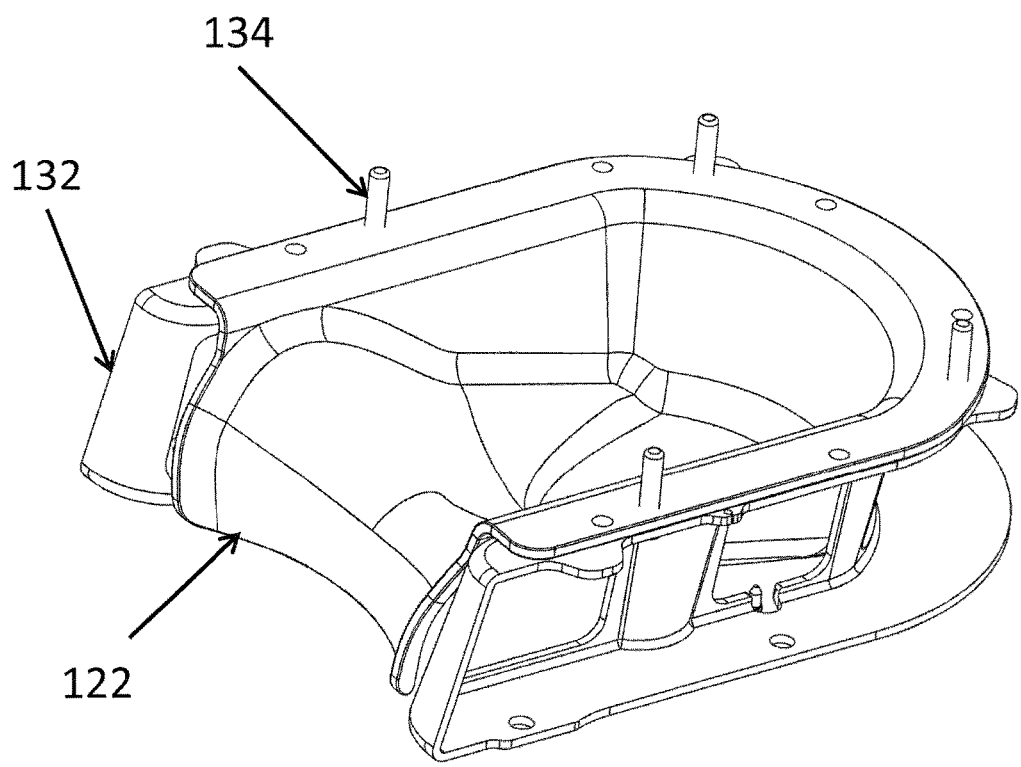
FIG. 13 is an isometric view of a cushion retaining device with a secondary structure in accordance with aspects of the invention.

FIG. 13 depicts a patient a cushion retaining device with a secondary structure according to embodiments of the invention. As shown, the cushion retaining device 122 is positioned above the secondary structure 132. Pins 134 may be used to index the cushion retaining device 122. When a cushion (e.g., cushions 10, 20, 30, 85, 90, 102 and 116) is formed, it contours to the back of a patient's head and to the cushion retaining device 122. This contour of the cushion retaining device 122 then ensures that the cushion is placed in the same position when the patient returns for subsequent treatment. The cushion retaining device 122 may be contoured to coincide with the anatomy of a patient. Additional features as described above may be provided to index the cushion to the cushion retaining device 122. Because the cushion retaining device 122, along with the secondary structure 132, support the cushion on the majority of the cushion's sides it reduces the resistance to movement of the patient.

Methods for producing heat formable patient positioning cushions are now described in accordance with embodiments of the invention. Generally, however, a method of producing a heat formable patient positioning cushion is provided, the cushion having a first condition configured to be conformed to the anatomy of a patient and a second condition conformed to the anatomy of the patient. The method includes mixing thermoplastic material with filler material; enclosing the mixture of thermoplastic material and filler material within an interior region of an outer shell such that heating and cooling changes the cushion from the first condition, in which the filler material moves relatively freely within the interior region of the outer shell, to the second condition, in which the filler material is relatively fixed against movement within the interior region of the outer shell, and such that reheating permits increased movement of the filler material as compared to the second condition to further conform the cushion to the anatomy of the patient.

The method can include additional steps. For example, the method can optionally include mixing thermoplastic material with discrete pieces of filler material or mixing thermoplastic material with fibers of filler material. If fibers are used, the method can include dicing the fibers into pieces 0.5 mm to 10 mm in length. The method can also include applying the thermoplastic material to the filler material as a coating or to an interior surface of the outer shell as a coating or a laminate.

If a fibrous filler material is used in the cushion, the method optionally includes impregnating a bonding material into a fibrous base material. If so, the method can also include heating and compressing the mixture into a thinned configuration such that, upon subsequent application of heat, the thermoplastic melts and allows the lofted fibrous material to expand.

The thermoplastic materials and filler materials used in the manufacturing methods may be substantially similar to the thermoplastic materials and filler materials described above with respect to FIGS. 1-13. The cushions may have a first condition configured to be conformed to the anatomy of a patient and a second condition conformed to the anatomy of the patient. In an embodiment, thermoplastic material is mixed with filler material. The thermoplastic material may be PCL, EVA, wax, paraffin wax, etc. The thermoplastic material mixed with the filler material has a melting temperature of about 200 F or higher, and optionally about 100 F or higher, depending on the material selected. The filler material may include polystyrene, PCL, foam, fibers, lofted felts, lofted felts impregnated with thermoplastic material, etc. Other suitable thermoplastic materials and filler materials will be understood by one of skill in the art from the description herein.

The filler material may comprise discrete pieces, such as solid spheres, hollow spheres, conical shaped pieces, pyramidal shaped pieces, cubic shaped pieces, etc. Additionally, or alternatively, the filler material may include pieces of fibers, lofted felt, and/or lofted felt impregnated with thermoplastic material or other fibrous materials. In embodiments where the filler material includes fibers, the fibers may be diced into pieces of about 0.5 mm to about 10 mm in length. In an embodiment, the mixture of fiber or lofted felt filler material and thermoplastic material are heated and compressed into a thinned configuration such that, upon subsequent application of heat, the thermoplastic melts and allows the lofted felt material to expand.

Prior to or following the mixing step, thermoplastic material may be applied to the filler material as a coating. Alternatively, or additionally, a thermoplastic material may be applied to an interior surface of an outer shell.

The filler material mixed with the thermoplastic material may then be enclosed within an interior region of an outer shell. The filler material may be enclosed such that heating and cooling of the interior region changes the cushion from the first condition to the second condition. In the first condition, the filler material moves relatively freely within the interior region of the outer shell in embodiments where the filler material includes discrete pieces and/or fiber, felt, impregnated lofted felt pieces. In the second condition, the filler material is relatively fixed against movement within the interior region of the outer shell. The filler material may be configured such that reheating the cushion in the second condition permits limited movement of the filler material, allowing the cushion in the second condition to be modified after the cushion has been changed to the second condition.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A heat formable patient positioning cushion consisting of a plurality of discrete pieces of filler material coated in a low melting temperature thermoplastic resin (melting temperature below 200° F.), said discrete pieces of filler material being contained in an outer casing.

2. A cushion of claim 1 in which the discrete pieces of filler material is at least one of; a polystyrene bead, a hollow polymer sphere, a hollow polymer microsphere.

3. A cushion of claim 1 in which the shape of the discrete pieces of filler material is at least one of; spherical, cubic, cylindrical, conical, pyramidal, irregular.

4. A cushion of claim 1 in which the low melting temperature thermoplastic resin is polycaprolactone.

5. A cushion of claim 1 in which the discrete pieces of filler material are individually precoated with the low temperature thermoplastic resin such that the discrete pieces of filler material do not initially stick to each other.

6. A cushion of claim 1 in which the outer casing is one of; (1) a water impermeable material such that hot water may be used to soften the low melting temperature thermoplastic without filling the space between the beads and (2) a permeable surface such that air may flow between the discrete pieces of filler material allowing all of the discrete pieces of filler material to become hot in a short period of time while still containing the discrete pieces of filler material within, said permeable area to be greater than 20% of the surface area.

7. A cushion of claim 1 in which the inner filler is not stuck to itself, therefore the cushion is initially pliable for forming prior to applying heat.

8. A heat formable patient positioning cushion comprising:
an impermeable or permeable outer shell;
a filler material contained within an interior region defined by the outer shell;
a thermoplastic material applied to the outer shell, to the filler material, or to the outer shell and the filler material;
wherein the cushion has a first condition configured to be conformed to the anatomy of a patient in which the filler material moves relatively freely within the interior region defined by the outer shell, and a second condition configured to be conformed to the anatomy of the patient in which the filler material is relatively fixed against movement within the interior region defined by the outer shell; and
wherein heating and cooling changes the cushion from the first condition to the second condition.

9. The heat formable patient positioning cushion of claim 8, the filler material comprising discrete pieces.

10. The heat formable patient positioning cushion of claim 9, wherein the discrete pieces include solid or hollow spheres.

11. The heat formable patient positioning cushion of claim 8, the filler material comprising polystyrene.

12. The heat formable patient positioning cushion of claim 8, the filler material comprising fibers.

13. The heat formable patient positioning cushion of claim 12, wherein the fibers form a lofted felt.

14. The heat formable patient positioning cushion of claim 13, the lofted felt being impregnated with the thermoplastic material.

15. The heat formable patient positioning cushion of claim 14, the impregnated lofted felt being compressed such that, upon application of heat, the thermoplastic material melts and allows the lofted felt to expand.

16. The heat formable patient positioning cushion of claim 12, the fibers being diced into pieces 0.5 mm to 10 mm in length.

17. The heat formable patient positioning cushion of claim 8, the outer shell being permeable to gas to facilitate heat transfer to the interior region of the outer shell, at least 20% of the surface area of the outer shell being formed from permeable material.

18. The heat formable patient positioning cushion of claim 8, the outer shell being impermeable to facilitate at least one of a vacuum applied to the interior region of the outer shell and heating the cushion with a fluid.

19. The heat formable patient positioning cushion of claim 18, further comprising a port positioned in the outer shell to apply the vacuum within the interior region of the outer shell.

20. The heat formable patient positioning cushion of claim 18, wherein the outer shell is impermeable to gas.

21. The heat formable patient positioning cushion of claim 18, wherein the outer shell is impermeable to water to facilitate heating the cushion with heated water.

22. The heat formable patient positioning cushion of claim 8, the thermoplastic material being applied to the filler material as a coating.

23. The heat formable patient positioning cushion of claim 8, the thermoplastic material being applied to an interior surface of the outer shell as a coating or a laminate.

24. The heat formable patient positioning cushion of claim 8, wherein the thermoplastic material has a melting temperature of less than 200° F.

25. The heat formable patient positioning cushion of claim 8, wherein the thermoplastic material includes one or more of polycaprolactone, ethylene vinyl acetate (EVA) and wax.

26. The heat formable patient positioning cushion of claim 8, wherein reheating the cushion in the second condition permits increased movement of the filler material as compared to the second condition to further conform the cushion to the anatomy of the patient.

* * * * *